(12) United States Patent
Berg

(10) Patent No.: US 7,412,288 B2
(45) Date of Patent: Aug. 12, 2008

(54) TEXT TO SPEECH CONVERSION IN HEARING SYSTEMS

(75) Inventor: Christian Berg, Uerikon (CH)

(73) Assignee: Phonak AG, Staefa (CH)

( * ) Notice: Subject to any disclaimer, the term of this patent is extended or adjusted under 35 U.S.C. 154(b) by 0 days.

(21) Appl. No.: 10/841,829

(22) Filed: May 10, 2004

(65) Prior Publication Data

US 2005/0251224 A1 Nov. 10, 2005

(51) Int. Cl.
*A61N 1/36* (2006.01)

(52) U.S. Cl. ........................................ 607/57

(58) Field of Classification Search ............. 607/55–57, 607/136–137; 600/379; 381/312, 328
See application file for complete search history.

(56) References Cited

U.S. PATENT DOCUMENTS

| | | | | |
|---|---|---|---|---|
| 4,532,930 | A * | 8/1985 | Crosby et al. | 607/57 |
| 5,403,262 | A * | 4/1995 | Gooch | 600/28 |
| 5,659,621 | A * | 8/1997 | Newton | 381/312 |
| 5,721,783 | A | 2/1998 | Anderson | |
| 6,073,100 | A * | 6/2000 | Goodridge, Jr. | 704/258 |
| 6,354,299 | B1 * | 3/2002 | Fischell et al. | 128/899 |
| 6,377,925 | B1 | 4/2002 | Greene, Jr. et al. | |
| 6,390,971 | B1 * | 5/2002 | Adams et al. | 600/25 |
| 6,394,947 | B1 * | 5/2002 | Leysieffer | 600/25 |
| 6,592,512 | B2 * | 7/2003 | Stockert et al. | 600/25 |
| 6,704,699 | B2 * | 3/2004 | Nir | 704/2 |
| 6,728,385 | B2 | 4/2004 | Kvaløy et al. | |
| 2002/0012438 | A1 * | 1/2002 | Leysieffer et al. | 381/312 |
| 2002/0029146 | A1 | 3/2002 | Nir | |
| 2004/0077382 | A1 * | 4/2004 | Verity | 455/569.1 |
| 2004/0202291 | A1 * | 10/2004 | Skinner | 379/67.1 |
| 2004/0203613 | A1 * | 10/2004 | Zhu et al. | 455/412.1 |
| 2005/0043951 | A1 * | 2/2005 | Schurter | 704/270.1 |
| 2005/0086058 | A1 * | 4/2005 | Lemelson et al. | 704/270 |
| 2005/0132292 | A1 * | 6/2005 | Nien | 715/718 |
| 2005/0176454 | A1 * | 8/2005 | Chakraborty et al. | 455/518 |

FOREIGN PATENT DOCUMENTS

| | | |
|---|---|---|
| WO | WO 96/41498 | 12/1996 |
| WO | WO 97/01314 | 1/1997 |

* cited by examiner

*Primary Examiner*—George R Evanisko
(74) *Attorney, Agent, or Firm*—David S. Safran

(57) ABSTRACT

A hearing system for a person, comprising: an input device for providing electrical signals produced from sound, a signal processor for processing said electrical signals for producing audio signals, a digital text storage for storing digital text received from a source of digital text, a converter for converting digital text from said digital text storage into audio signals, and an output transducer for converting audio signals into a stimulation of a person's hearing. The hearing system is designed to be worn at least partly within the person's ear canal or behind the person's ear or is designed to be at least partially implanted within the person's skull.

36 Claims, 2 Drawing Sheets

TEXT TO SPEECH CONVERSION IN HEARING SYSTEMS

BACKGROUND OF THE INVENTION

1. Field of the Invention

The present invention relates to a hearing system for a person, comprising input means for providing electric signals, signal processing means for processing the electrical signals for producing audio signals and output transducer means for converting audio signals into a stimulation of the person's hearing. The invention also relates to a method for operating a hearing system.

2. Description of Related Art

From WO 97/01314 a hearing system is known which comprises a microphone, a microprocessor for signal processing and a cochlear electrode array disposed adjacent to the basilar membrane. These components may be integrated within an implanted housing or the microphone and the microprocessor may be integrated within a separate external unit which is connected to the electrode array via a wireless link. The system further includes an external remote control keypad connected to the microprocessor via a wireless link. The keypad serves to enter commands for controlling operation of the hearing system. The system further includes a message source consisting of a message memory and a speech synthesizer for transmitting messages to the user of the system. The messages are entered into the system via the microphone and are processed by a speech processor prior to being stored in the message memory.

U.S. Pat. No. 5,721,783 discloses a hearing system comprising an ear piece which is to be arranged in the ear canal and a remote processor unit which can be concealed under clothing and which communicates with the ear piece via a wireless link. The ear piece comprises a microphone, a transmitter and a speaker, while the remote processor unit provides for processing of audio signals. The remote processor unit may be connected to a remote-site computer via a secondary wireless link for exchanging both digital data and speech signals. Thereby the hearing system facilitates text-to-speech translation of electronic mail messages and faxes where information is received via the secondary link and processed by the digital signal processor of the remote processor unit.

U.S. 2002/0012438 A1 relates to a hearing system comprising a speech recognition module and a speech synthesis module as the signal processing unit between the input transducer and the output transducer, with the output of the speech recognition module being input into the speech synthesis module, whereby an effective reduction of noise is achieved.

It is an object of the invention to provide for a hearing system which is able to provide external information, such as messages, shopping lists etc. to the user without requiring large memory capacities. It is a further object to provide for a corresponding method for operating a hearing system.

SUMMARY OF THE INVENTION

According to the present invention these objects are achieved by a hearing system as defined in claim 1 and a method as defined in claim 33. This solution is beneficial in that by inputting and storing information as digital text in the hearing system prior to converting the digital text into audio signals, text information to be provided to the person using the hearing system is handled and stored in a very compact manner, so that in particular the storing means only need to have a significantly reduced capacity compared to storage of information as audio signals. Thereby the functionality of conventional hearing systems can be significantly enhanced without the need of a significantly increased system complexity.

The input means may be a microphone. Alternatively, the input means may be an input receiver means for receiving electrical signals from an external signal source, such as an external microphone, preferably via a wireless link.

The source of digital text may be external to the hearing system, with hearing system comprising an interface for communication with the external source of digital text. Alternatively, the source of digital text may be internal to the hearing system and comprises means for converting speech to digital text. In addition, also combined embodiments are perceivable, wherein the digital text to be stored is provided both from an external source and from an internal source.

The signal processing means may be adapted to provide for a hearing aid function of the hearing system, e.g. by amplifying the electrical signals. Alternatively or in addition, the signal processing means may be adapted to provide for an active hearing protection function of the hearing system.

The hearing system may comprise means for recognizing specific pre-defined non-speech sounds, means for associating a specific digital text stored in the text storage means to each of the pre-defined non-speech sounds, and means for retrieving a specific digital text associated to the recognized pre-defined non-speech sound form the text storage means and providing it to said means for converting digital text into audio signals. For example, the pre-defined non-speech sounds comprise alarm signals, with the associated specific digital text comprising alarm messages. Thereby the user may be safely provided, for example, with an alarm message while protected from a noisy auditory scene. Preferably the text converting means comprise a programmable digital signal processor and a program memory with a speech synthesis software which may be input into the hearing system from a programming unit via the interface.

The interface may be adapted for wireless communication based on the Bluetooth standard.

Preferably the source of digital text is a Personal Digital Assistant (PDA), a portable computer (i.e. a notebook or a laptop), a personal computer or a mobile phone.

Preferably, the hearing system is adapted for communication with external fitting means designed for performing at least one of the following functions: determining the language and/or the speaker of the audio signals converted from the digital text; adjusting the loudness of the audio signals produced by the digital text converting means; activation or deactivation of the digital text converting means; controlling mixing of the audio signals produced by the digital text converting means with the audio signals produced by the signal processing means from the input electrical signals. The fitting means may be implemented in the text source or in the programming unit or in a separate device, such as a personal computer or a Personal Digital Assistant.

These and further objects, features and advantages of the present invention will become apparent from the following description when taken in connection with the accompanying drawings which, for purposes of illustration only, show several embodiments in accordance with the present invention.

Figure 1:
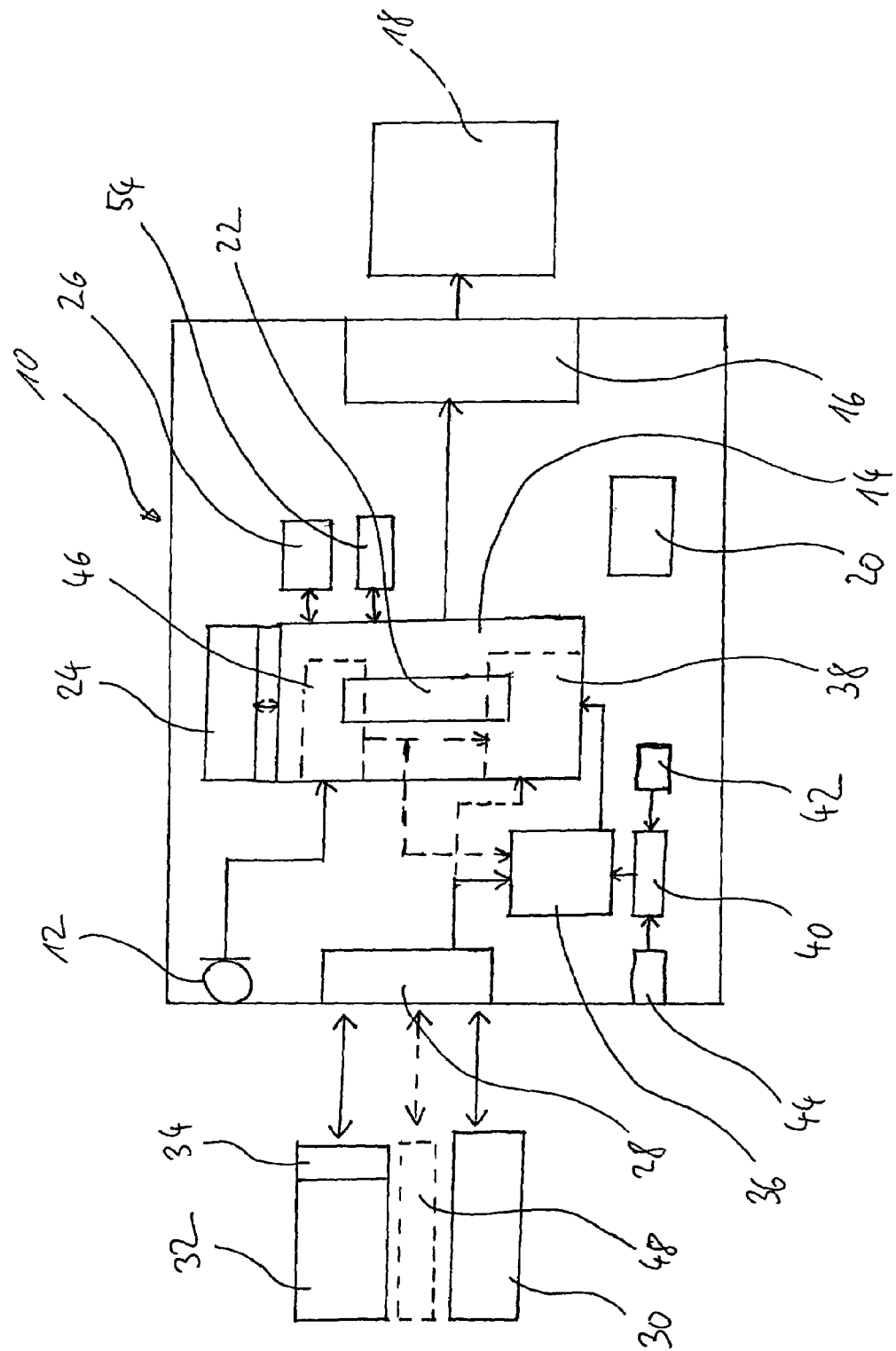
FIG. 1 shows a schematic block diagram of an example of a hearing system according to the invention.

According to the embodiment of FIG. 1, a hearing system 10 comprises input transducer means 12 for converting ambient sounds into an electrical signal, signal processing means 14 for processing the electrical signals of the input transducer means 12 for producing audio signals and output transducer means 16 for converting audio signals into a stimulation of a person's hearing 18.

Usually the input transducer means is a microphone 12. The output transducer means is preferably an electro-acoustic transducer, i.e. a speaker, which is located in the ear canal. Alternatively, the output transducer means may be, for example, a cochlear electrode array disposed adjacent the basilar membrane for direct electrical stimulation of the cochlear nerve of the person's ear 18 or an electromechanical transducer for stimulation of the middle ear or the inner ear of the person. In the case of an electro-acoustic transducer, the hearing system 10 is designed to be worn in the person's ear canal ("in-the-ear") or behind the person's ear ("behind-the-ear"). In the other cases, the hearing system 10 will be at least partially implanted in the person's skull, with at least the output transducer means 16 being implanted.

The hearing system 10 further includes a power supply 20, i.e. a rechargeable or non-rechargeable battery.

According to FIG. 1, the signal processing means 14 includes a programmable digital signal processor (DSP) 22 and a program memory 24 wherein a control program for the DSP 22 is stored. In addition, a data memory 26 is provided wherein person-specific data needed by the control program for operating the hearing system 10 is stored.

The hearing system 10 further includes an interface 28 for wireless communication with an external programming unit 30 which serves to individually adapt the hearing system 10 to the person by inputting person-specific data into the data memory 26. In addition, the programming unit 30 may serve to update the control software in the program memory 24.

Preferably, the interface 28 is adapted for wireless communication based on the so-called "Bluetooth" standard, for example a standard available under the trademark "NOAHLink".

The components described so far may also form part of a conventional hearing system. By contrast, the features described in the following are specific to embodiments of the present invention.

The interface 28 is also adapted for wireless communication not only with the programming unit 30 but also with a source 32 of digital text which preferably is a Personal Digital Assistant (PDA), a portable computer such as a laptop or a notebook, a non-portable personal computer or a mobile phone. Preferably, communication between the text source 32 and the interface 28 uses the same standard as the communication between the programming unit 30 and the interface 28. This can be achieved, for example, by providing the text source 32 with an appropriate added device 34, such as a plug-in USB device or personal computer card device.

Digital text received from the text source 32 is stored in a non-volatile text memory 36. The signal processing means 14 includes means 38 for converting digital text received from the text memory 36 into audio signals which are converted by the output transducer means 16 into a stimulation of the person's ear 18. The text converting means 38 are represented by a speech synthesis function provided by the DSP 22 in combination with a corresponding speech synthesis software stored in the program memory 24. For initiating speech synthesis, the digital text output from the text memory 36 is controlled by activation means 40 which, in turn, may be controlled or activated by a timer 42 or operating means 44 to be operated by the person. The operating means may be represented, for example, by a manual switch or a voice control module.

The audio signals produced by speech synthesis may be mixed with the audio signals produced from the signals of the microphone 12, or may be provided to the output transducer 16 alternately with the audio signals produced from the signals of the microphone 12. As indicated by a dashed line in FIG. 1, the text converting means 38 also my be capable of receiving and converting the digital text input received directly from the interface 28 and not stored in the text memory 36.

Preferably, the hearing system 10 is adapted for communication with external fitting means designed for performing at least one of the following functions: determining the language and/or the speaker of the audio signals converted from the digital text, adjusting the loudness of the audio signals produced by the digital text converting means 38, activation or deactivation of the digital text converting means 38, and controlling the mixing of the audio signals produced by the digital text converting means 38 with the audio signals produced by the signal processing means 14 from the input electrical signals (e.g. controlling the loudness ratio of the two signals). The fitting means may implemented in the text source 32 or in the programming unit 38. Alternatively, the fitting means may be implemented in a separate device 48, such as a personal computer, a Personal Digital Assistant or a mobile phone, which communicates with hearing system 10 via the interface 28, preferably via a wireless link.

In addition, the signal processing means 14 may include means 46 for voice and/speech recognition in order to achieve a significantly improved signal to noise ratio by converting the electrical signal from the microphone 12 into text by the speech recognition means 46 and recreating speech (i.e. an audio signal corresponding to speech) by the speech synthesis function 38.

The digital text provided by the text source 32 may be all kind of messages and information, such as telephone numbers, addresses, shopping lists, agenda information etc. By using the timer 42 such information may be provided by the hearing system 10 the person's ear 18 at a given time as a reminder. Alternatively, the desired text information may be retrieved by the person from the text memory 36 by acting on the operating means 44.

In a modified embodiment, if this is desired for some reason, a separate interface may be provided for the text source 32 and the speech synthesis function 38 may be provided separate from the signal processing means 14.

Figure 2:
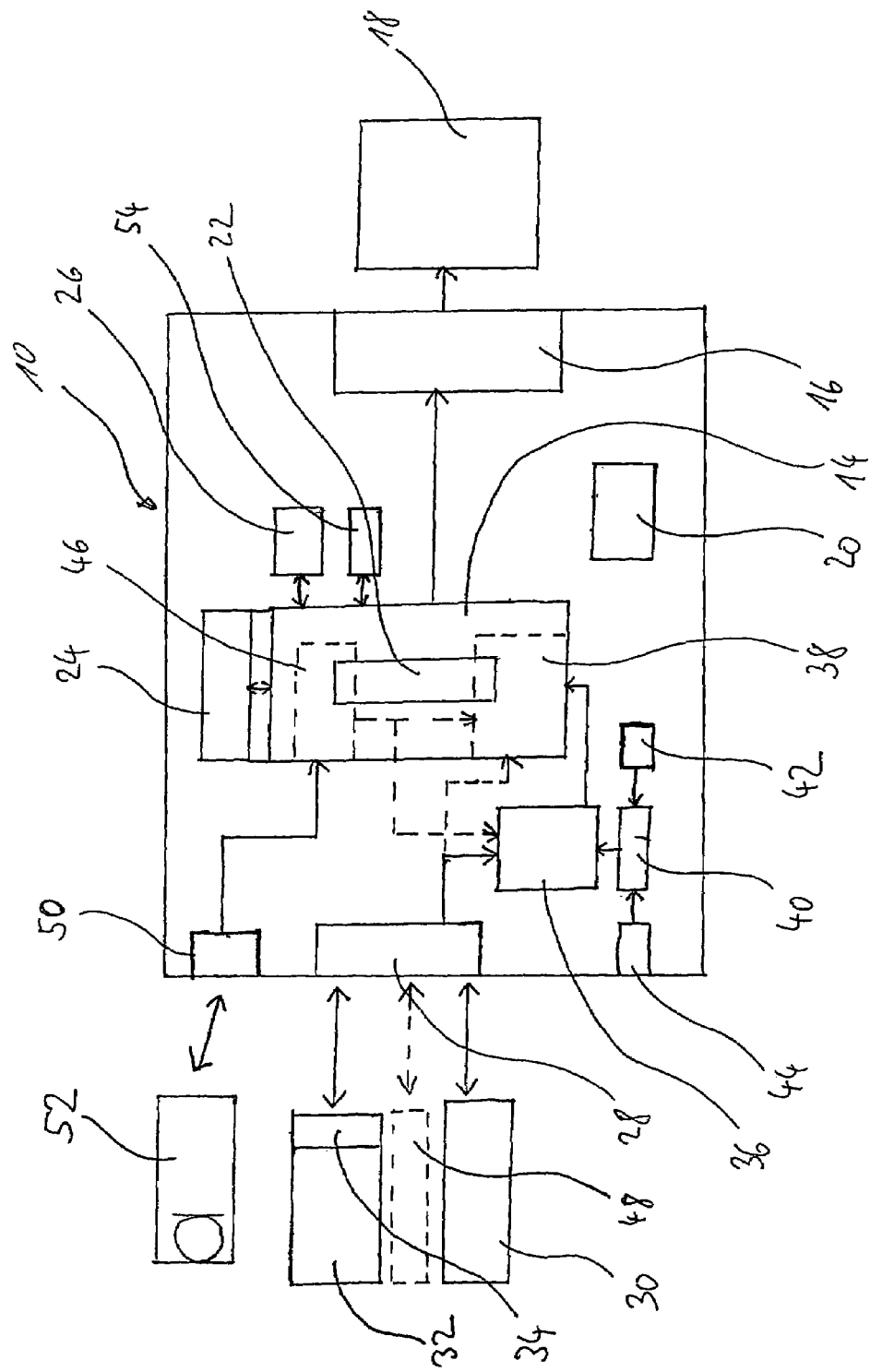
FIG. 2 shows a schematic block diagram of an alternative example of a hearing system according to the invention.

FIG. 2 shows an alternative embodiment which differs from the embodiment of FIG. 1 in that the microphone 12 internal to the hearing system 10 is replaced by an input receiver means 50 for receiving electrical input signals from an external signal source 52, such as an external microphone, via a wireless link, such as a RF link.

Such a configuration may be employed, for example, for the wireless communication between persons in a noisy environment, such as in an air plane or on a boat. In this case the external signal source 52 is a microphone worn by another person. The hearing system 10 may be integrated within a noise protection device worn at or within the user's ear.

In another modified embodiment, the external digital text source 32 may be supplemented of replaced by an internal digital text source formed by the speech recognition means 46 where selected speech signals received from the microphone 12 or the input receiver means 50 are converted to digital text which can be stored in the text memory 36 for later, e.g. upon request by the user, being retrieved by the activation means 40 and reconverted to audio signals by the speech synthesis function 38.

According to one embodiment, the hearing system 10 includes a hearing aid function, in particular for use by persons having an impaired hearing. To this end, the signal processing means 14 is adapted to provide for a hearing aid function, e.g. by amplifying and person-specifically modifying the electrical signals provided by the microphone 12 or the input receiver means 50.

Alternatively or in addition, the hearing system 10 may include an active hearing protection function. To this end, the signal processing means 14 may be adapted to attenuate the electrical signals provided the microphone 12. In this respect, the signal processing means 14 may include a sound analyzing processor for controlling the active hearing protection function depending on the analyzed auditory scene. For example, in a silent environment no attenuation will take place, while in a noisy environment attenuation will be applied with an appropriate level depending on the noise level. Alternatively, the signal processing means 14 may be adapted to invert the electrical signals provided by the microphone 12 in phase for producing "anti-noise" in order to reduce the noise level.

In general, signal processing means 14 system may comprise means for recognizing specific pre-defined non-speech sounds, means for associating a specific digital text stored in the text memory 36 to each of the pre-defined non-speech sounds, and means for retrieving a specific digital text associated to the recognized pre-defined non-speech sound from the text memory 36 and providing it to the means 38 for converting digital text into audio signals. For example, the pre-defined non-speech sounds may comprise alarm signals, with the associated specific digital text comprising corresponding alarm messages. Thereby the user may be safely provided, for example, with an alarm message while protected from a noisy auditory scene. This feature is particularly beneficial for being used together with the active hearing protection function, but may also be used together with the hearing aid function.

Preferably, the signal processing means 14 is adapted to mix the audio signals produced from the associated specific digital text with audio signals produced from electrical signals of microphone 12 or the input receiver means 50.

The hearing system may include means 54 for storing pre-defined non-speech sounds which are pre-recorded.

The signal processing means 14 may include means for controlling operation of the hearing system 10 according to pre-defined speech commands detected by the speech recognition means 46, thereby enabling voice control of the hearing system 10. Alternatively or in addition signal processing means 14 may include means for recognizing specific pre-defined non-speech sound commands and means for controlling operation of the hearing system according to the pre-defined non-speech sound commands when detected.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A hearing system for a person, comprising:
   input means for providing electrical signals produced from sound,
   signal processing means for processing said electrical signals for producing audio signals,
   means for storing digital text representative of text information to be provided to said person and received from a source of the digital text,
   means for converting the digital text from said text storing means into speech audio signals, and
   output transducer means for converting the audio signals produced by the signal processing means and the speech audio signals produced by the means for converting digital text into a stimulation of said person's hearing,
   wherein said hearing system is sized to fit at least partly within the person's ear canal or behind the person's ear or be at least partially implanted within the person's skull; and
   wherein the text converting means comprise a programmable digital signal processor and a program memory with a speech synthesis software for converting the digital text into speech audio signals.

2. The hearing system of claim 1, wherein said source of the digital text is external to said hearing system and wherein said hearing system comprises an interface for communication with said external source of digital text.

3. The hearing system of claim 2, wherein said interface is adapted for wireless communication.

4. The hearing system of claim 3, wherein said interface is adapted for wireless communication based on the Bluetooth standard.

5. The hearing system of claim 4, further comprising means for controlling operation of said hearing system according to pre-defined speech commands recognized by said means for converting speech to said digital text. electrical signals.

6. The hearing system of claim 2, wherein said means for converting the digital text from said storing means are also adapted to convert the digital text from said interface into audio signals.

7. The hearing system of claim 1, wherein said input means is an input transducer for converting ambient sounds into said electrical signals.

8. The hearing system of claim 1, wherein said input means is an input receiver means for receiving electrical signals from an external signal source.

9. The hearing system of claim 8, wherein said input receiver means is adapted to be connected to said external signal source via a wireless link.

10. The hearing system of claim 9, wherein a microphone is provided for converting ambient sounds into said electrical signals as said external signal source.

11. The hearing system of claim 1, wherein said hearing system is adapted for communication with external fining means designed for performing at least one function selected from the group consisting of:
    determining a language of said audio signals converted from said digital text,
    determining a speaker of said audio signals converted from said digital text,
    adjusting a loudness of said audio signals produced by said digital text converting means,
    activating said digital text converting means, deactivating said digital text converting means, and
    controlling a mixing of said audio signals produced by said digital text converting means with said audio signals produced by said signal processing means from said input electrical signals.

12. The hearing system of claim 11, wherein said hearing system is adapted for communication with said external fining means via an interface.

13. The hearing system of claim 11, further comprising at least one of said text source, an external programming unit and an external personal computer or Personal Digital Assistant for serving as the fining means.

14. The hearing system of claim 1, wherein said signal processing means comprise said programmable digital signal processor and said program memory, said program memory comprising a control software, and wherein means for storing person-specific data used by said control software are provided.

15. The hearing system of claim 14, wherein said source of the digital text is external to said hearing system and wherein said hearing system comprises an interface for communication with said external source of digital text, and wherein said interface is designed to input at least one of said speech synthesis software, said control software and said person-specific data into said hearing system from an external programming unit.

16. The hearing system of claim 1, further comprising one of a Personal Digital Assistant, a portable computer, a personal computer, and a mobile telephone as the source of said digital text.

17. The hearing system of claim 1, further comprising activation means for initiating conversion of digital text from said text storing means into audio signals, said activation means being adapted to be controlled by a timer or by operating means adapted to be operated by said person.

18. The hearing system of claim 1, wherein said signal processing means comprises means for speech recognition.

19. The hearing system of claim 18, wherein said speech recognition means are adapted to convert speech into the digital text and wherein an output of said speech recognition means is connected to said means for converting the digital text into audio signals.

20. The hearing system of claim 1, wherein said output transducer means is selected from the group consisting of an electro-acoustic transducer, an electromechanical transducer for stimulation of a middle ear, an electromechanical transducer for stimulation of an inner ear, and a cochlear electrode array for direct electrical stimulation of a cochlear nerve.

21. The hearing system of claim 1, further comprising a means for converting speech to the digital text located within the hearing system as the source of said digital text.

22. The hearing system of claim 1, wherein said signal processing means are adapted to provide for a hearing aid function of said hearing system.

23. The hearing system of claim 1, wherein said signal processing means are adapted to invert said electrical signals provided by said input means in phase for providing for an active hearing protection function of said hearing system.

24. The hearing system of claim 23, further comprising a sound analyzing processor for controlling said active hearing protection function depending on an analyzed auditory scene.

25. The hearing system of claim 1, wherein said signal processing means are adapted to attenuate said electrical signals provided by said input means in phase for providing for an active hearing protection function of said hearing system, said attenuation depending on a noise level detected by said hearing system.

26. The hearing system of claim 1, further comprising means for recognizing specific pre-defined non-speech sounds, means for associating a specific digital text stored in said text storage means to each of said pre-defined non-speech sounds, and means for retrieving a specific digital text associated to said recognized pre-defined non-speech sound from said text storage means and providing said specific digital text to said means for converting digital text into audio signals.

27. The hearing system of claim 26, wherein said pre-defined non-speech sounds comprise alarm signals, with said associated specific digital text comprising alarm messages.

28. The hearing system of claim 26, further comprising means for storing said pre-defined non-speech sounds.

29. The hearing system of claim 26, wherein said signal processing means is adapted to mix said audio signals produced from said associated specific text with audio signals produced from said electrical signals of said input means.

30. The hearing system of claim 1, further comprising means for recognizing specific pre-defined non-speech sound commands and means for controlling operation of said hearing system according to said pre-defined non-speech sound commands detected by said means for recognizing specific pre-defined non-speech sound commands.

31. The hearing system of claim 1, wherein said output transducer means comprises means for stimulation of said person's hearing by one of direct electrical stimulation of the cochlear and electromechanical stimulation of the middle or inner ear.

32. A method for operating a hearing system which is worn at least partly within a person's ear canal or behind a person's ear or is at least partially implanted within a person's skull, comprising:
   inputting digital text from a source into said hearing system,
   storing the digital text representative of text information to be provided to said person and received from said source of the digital text within said hearing system,
   converting the stored digital text into speech audio signals,
   converting ambient sounds into electrical signals within the hearing system,
   processing said electrical signals for producing speech audio signals and converting the audio signals converted from ambient sounds and the audio signals converted from the stored digital text into a stimulation of said person's hearing;
   wherein the converting of the stored digital text into audio signals is performed by a programmable digital signal processor and a program memory using speech synthesis software for converting digital text into speech audio signals.

33. The method of claim 32, further comprising:
   mixing said audio signals produced from said digital text with said audio signals produced from converted ambient sounds.

34. The method of claim 32, wherein said digital text is input from an external source.

35. A method for operating a hearing system which is worn at least partly within a person's ear canal or behind a person's ear or is at least partially implanted within a person's skull, comprising:
   inputting digital text from a source into said hearing system,
   storing the digital text received from said source of the digital text within said hearing system, converting the stored digital text into audio signals,
   converting ambient sounds into electrical signals within the hearing system,
   processing said electrical signals for producing audio signals and converting the audio signals converted from ambient sounds and the audio signals converted from the stored digital text into a stimulation of said person's hearing further comprising:

converting speech to digital text within said hearing system as said digital text source.

36. The method of claim 32, wherein said stimulation of said person's hearing is produced by one of direct electrical stimulation of the cochlear and electromechanical stimulation of the middle or inner ear.

* * * * *